United States Patent [19]

Davis, Jr.

[11] Patent Number: 4,560,816
[45] Date of Patent: Dec. 24, 1985

[54] CATALYZED HYDROGENATION AND DEHYDROGENATION PROCESSES

[75] Inventor: Milton W. Davis, Jr., Lexington, S.C.

[73] Assignee: University of South Carolina, Columbia, S.C.

[21] Appl. No.: 546,065

[22] Filed: Oct. 27, 1983

Related U.S. Application Data

[60] Continuation of Ser. No. 383,786, Jun. 1, 1982, abandoned, which is a continuation of Ser. No. 309,768, Oct. 8, 1981, abandoned, which is a continuation of Ser. No. 114,556, Jan. 23, 1980, abandoned, which is a division of Ser. No. 801,388, May 27, 1977.

[51] Int. Cl.$^4$ .............................................. C07C 5/10
[52] U.S. Cl. .................................. 585/266; 208/143; 585/661
[58] Field of Search ........................ 585/266; 208/143

[56] References Cited

U.S. PATENT DOCUMENTS 2,373,501 4/1945 Peterson .............................. 588/266
3,865,750 2/1975 Rase et al. ............................ 588/266
4,139,551 2/1979 Ozyagcilat ........................ 260/449.5

Primary Examiner—D. E. Gantz
Assistant Examiner—Chung K. Pak
Attorney, Agent, or Firm—Brumbaugh, Graves, Donohue & Raymond

[57] ABSTRACT

Titanium-iron alloys, conditioned or activated to be reversible hydride formers, function as catalysts to promote gas phase hydrogenation and, dehydrogenation reactions. In the hydride form in the presence of hydrogen, the alloys catalyze hydrogenation of C≡C, C=C, C=O, C=O, C=N, C≡N, N=O, N=N and N≡N bonds. Of particular utility is the synthesis of ammonia from a hydrogen-nitrogen mixture at relatively low temperature and pressure. In the unhydrided or metallic form the alloys dehydrogenate C—C, C=C, C—H and C—N bonds where hydrogen is attached to these groups. Of particular utility is the dehydrogenation of ethane to form ethylene at relatively low temperature and where increased pressure increases the percentage of ethane converted to ethylene.

1 Claim, No Drawings

CATALYZED HYDROGENATION AND DEHYDROGENATION PROCESSES

This application is a continuation of application Ser. No. 383,786, filed on June 1, 1982, now abandoned, which is a continuation of application Ser. No. 309,768, filed on Oct. 8, 1981, now abandoned, which is a continuation of application Ser. No. 114,556, filed Jan. 23, 1980, now abandoned, which is a division of application Ser. No. 801,388, filed May 27, 1977.

This invention relates to the use of titanium-iron alloys as catalysts in gas phase chemical reactions. In particular the invention relates to hydrogenation and dehydrogenation gas phase reactions catalyzed by such alloys.

BACKGROUND

One well-known gas phase hydrogenation reaction is the hydrogenation of nitrogen to form ammonia. This reaction is carried out on a large commercial scale by the Haber-Bosch process, or a modification, in which a gaseous mixture of hydrogen and nitrogen is passed in contact with a solid catalyst whereupon a portion of the hydrogen and nitrogen in the mixture reacts to form ammonia. The ammonia is removed from the resulting gas mixture by any of several techniques, and the unreacted hydrogen and nitrogen pass to a further catalytic reaction stage or are recycled to the same reaction stage.

It has long been recognized that the equilibrium yield for the reaction is high at low temperature and decreases as temperature increases. However, the rate of reaction at low temperature is very low, and even in the presence of the known catalysts for the reaction the temperature of the reaction must be high in order to effect a satisfactory rate of conversion. In order to compensate for the low equilibrium yield at the higher temperature, current commercial processes are operated at high pressure. Typically commercial ammonia production is carried out in the reactor generally in the range 350° C. to 560° C. at 100 atmospheres to 1000 atmospheres in the presence of a promoted iron catalyst. Conversion to ammonia from the stoichiometric mixture during one pass of the mixture through the reactor is generally in the range 15% to 25%. Typical equilibrium yields with stoichiometric quantities of hydrogen and nitrogen and no impurities are shown in the following table:

| Pressure, psi | Temp. °C. | Equilibrium Yield, % |
| --- | --- | --- |
| 500 | 300 | 9 |
| 500 | 200 | 50 |
| 1500 | 200 | 77 |
| 3000 | 300 | 52 |

It is apparent from these figures that if a catalyst which is active at lower temperatures can be developed, then very high yields can be obtained at low temperature. If the reaction pressure is maintained high, even high equilibrium yields are available and this would result in a significant advantage in terms of increased ammonia production rates. Alternatively, the pressure can be reduced to reduce energy costs while still maintaining a good production rate.

For many years the catalysts employed for the commercial production of ammonia have been promoted iron catalysts because these materials have been found to be both active and stable. Promoted iron is prepared by melting iron oxide, together with promoter components such as $Al_2O_3$, CaO, BaO, $K_2O$, $ZrO_2$, or $SiO_2$, cooling and crushing the resulting oxide, and then reducing the oxide with hydrogen to produce a granular porous iron structure containing the promoters in dispersed form. The material must be cleaned or conditioned before use, usually by heating it in the presence of hydrogen. A typical catalyst for ammonia production is a triply promoted iron containing 90 weight % iron and 10 weight % $Al_2O_3$, CaO and $K_2O$ having a surface area of 3 to 12 square meters per gram.

SUMMARY OF THE INVENTION

The present invention is based on the discovery that a family of titanium-iron alloys have catalytic properties which render them exceptionally well suited for use in gas phase hydrogenation and dehydrogenation reactions.

For purposes of this description, a Ti-Fe alloy means on alloy wherein titanium and iron together constitute the major proportion of the alloy in terms of atomic ratio. In general, the family of suitable alloys includes the binary alloys ternary and quaternary alloys having compositions corresponding to $Ti\ Fe_x\ Mg\ N_z$ where M and N are metals or compounds present in a relatively small amounts in a matrix of titanium iron alloy.

The family of titanium-iron alloys are not new and some of the members of the family have been investigated and used by others as hydrogen storage media. Titanium itself forms a relatively stable dehydride ($Ti\ H_2$) when reacted with hydrogen at room temperature provided that its surface is free of oxide. Some of the titanium-iron alloys, unlike titanium, have an exceptional ability to absorb hydrogen reversibly; that is, they are capable of absorbing very large amounts of hydrogen (to the extent that its density within the solid is about the same as liquid hydrogen) at relatively low temperature and are capable of releasing the hydrogen when heated to an elevated temperature. For example, the hydrogen vapor pressure is about 10 atm over $Ti_1\ Fe_1$ when the atom ratio $H/(Ti+Fe)$ is 0.5 at 55° C. The absorption and desorption cycle can be carried out many times and for this reason the alloys have been employed to store hydrogen and to release it when desired, for example to a fuel cell for generating electrical current or driving a hydrogenfueled internal combustion engine. The absorption of the hydrogen takes place as a result of titanium iron hydride ($Ti\ FeH$) formation, accompanied by the generation of heat which must be removed as the reaction continues. The reaction is reversible, so that liberation of hydrogen can be effected by heating the hydride to a higher temperature in order to cause decomposition. The mechanism of the absorption and desorption reactions forms no part of the present invention, but it is likely that the reactions themselves enter into the catalytic effect which is the basis of the invention.

Accordingly for the purposes of this description a Ti-Fe alloy also means a composition which can absorb and release hydrogen cyclically in large amounts, as a result of having been first conditioned, i.e., cleaned or activated, in order to remove contamination such as metal oxide surface deposits or small amounts of other gases. Conditioning has been accomplished in the past by a technique which involves alternately outgassing the alloy and then exposing the heated alloy to hydrogen under superatmospheric pressure. This conditioning technique or an analogous one is also required if the alloy is to exhibit catalytic properties and accordingly the present invention always contemplates that the alloy being used as a catalyst has been properly conditioned so as to be capable of reversible conversion between a metallic state and a hydride state. In the present invention the hydride form of the alloy is used, in the presence of hydrogen, for effecting hydrogenation reactions; the metallic form of the alloy, in the absence of hydrogen except as the latter is formed during reaction, for effecting dehydrogenation reactions.

Typically any solid catalyst regardless of its composition must be conditioned to render it useful for its intended purpose, and the conditioning step varies with the nature and composition of the catalyst. The present invention, therefore, does not depart from prior practice in this respect except that the conditioning step must of course be specific to titanium-iron alloys.

It has now been found that these Ti-Fe alloys, in the hydride form, and in the presence of hydrogen gas catalyze the hydrogenation of chemical bonds of the $C\equiv C$, $C=C$, $C=O$, $C=O$, $C\equiv N$, $C=N$, $N=O$, $N\equiv N$ and $N=N$ types, with the degree of hydrogenation depending on the reaction conditions and the particular alloy used. Examples of such reactions are the conversion of $N_2$ to $NH_3$, the conversion of $CO_2$ to $CH_4$, the conversion of CO to $CH_3OH$ and $CH_4$, the conversion of $C_2H_4$ to $C_2H_6$ and the conversion of benzene to cyclohexane. The ethylene to ethane reaction proceeds to completion rapidly (one minute) at 100° C. and 1000 psi with the $Ti_{1.1}Fe_1$ alloy used as the catalyst when hydrogen is present in large excess.

It has also been found that these Ti-Fe alloys, in the metallic or unhydrided form and in the absence of hydrogen gas other than that formed during reaction, catalyze the dehydrogenation of chemical bonds of the C—C, $C=C$, C—H and C—N types where hydrogen is attached to these groups with the degree of dehydrogenation depending on the reaction conditions and the particular alloy used. For example, ethane is dehydrogenated to ethylene and $H_2$ using the $Ti_{1.1}Fe_1$ alloy with the following results and conditions.

TABLE I

| Reaction Temp | Reaction Pressure | Reaction Time | % Conversion to $C_2H_4$ | % Conversion of $C_2H_6$ |
|---|---|---|---|---|
| 720° C. | 400 psia | 5 min. | 6.5% | 8.5% |

The 2% of ethane not converted to ethylene is converted to Methane and hydrogen with some carbon deposition. The reaction used for the dehydrogenation experiments was a 16 inch long −1 inch inside diameter tubular reactor made of 316 stainless steel. The volume of the catalyst bed was 180 cubic centimeters and it contained 365 grams of the $Ti_{1.1}Fe_1$ catalyst. The results reported were obtained using the reactor as a batch reactor. No continuous flow experiments have been performed.

For ammonia synthesis, which is one of the most important features of the present invention, it has been found that a $TiFe_2$ alloy produces essentially no ammonia whereas under the same reaction conditions ammonia is produced using as a catalyst TiFe, $Ti_{1.1}Fe$, $Ti_2Fe$, $Ti_3Fe$, $TiFe_{0.7}Mn_{0.2}$ and $TiFe_{0.9}Ni_{0.1}$. With respect to the binary alloys the amount of ammonia produced increases from substantial to large as the titanium content (atom ratio) of the alloy increases from 1.1:1 to 3:1.

With respect to ternary alloys containing large amounts of manganese or nickel as the third component the production of ammonia is not as large with the binary alloys of similar titanium/iron ratio; that is, the addition of manganese or nickel depresses the ammonia production rate although the amount of hydrogen absorbed by the ternary alloys is about the same as for the binary alloys.

With respect to the hydrogenation of carbon dioxide and carbon monoxide, it has been found that $Ti_{1.1}Fe$ is more effective than $Ti_3Fe$ for the conversion of carbon dioxide to methane and the conversion of carbon monoxide to methanol and/or ethane.

Referring again to the conditioning or activating of titanium-iron alloys to render them suitable as catalysts a typical technique includes placing a quantity of the alloy in a reactor vessel and carrying out the following steps:

(1) Heat the reactor to 400°–450° C. while simultaneously outgassing the alloy by applying a vacuum to the reactor to withdraw liberated gases. Continue outgassing for about one hour.

(2) Introduce hydrogen into the reactor under superatmospheric pressure of about 65 atmospheres while maintaining the elevated temperature for about 12 hours.

(3) Outgas the reactor and repeat the process until an infra-red analysis of the outgas shows no impurities in the hydrogen leaving the reactor.

(4) Cool the reactor to room temperature and introduce hydrogen into the reactor under superatmospheric pressure of about 65 atmospheres. A large temperature rise and a sharp drop in hydrogen pressure indicates that the alloy is in the hydride form and is ready for use in hydrogenation reactions. Exposure to air or oxygen will require the alloy to be reconditioned prior to use.

The time periods, temperatures and hydrogen pressures may vary widely, and the sequence of steps (1) through (4) may be repeated a number of times. The ability of the alloy to hydrogenate carbon dioxide and carbon monoxide is an advantage in the conditioning step because these gases may be present on the alloy. The alloy is considered to be conditioned when in step (4) or its equivalent a rapid rise in the temperature is a result of the reaction of the hydrogen with the Ti-Fe to produce the hydride TiFeH and of the reaction of the hydrogen with the excess titanium to produce $TiH_2$, particularly if the titanium is present in large excess. It is known that the increase in volume caused by the hydrogenation of the alloy produces a very large number of tiny cracks in the surface of the alloy and that this is in part responsible for the ability of the product to thereafter absorb and liberate hydrogen rapidly. Thus at the end of step (4) the product is in its hydride form, although of course if step (1) is repeated the product will be in metallic, dehydrided form. Both forms are encompassed by the term alloy as used in this description, because when the material is functioning as a catalyst it is not known whether or to what extent hydrogen is being absorbed or liberated.

The surface area of the catalyst available for exposure to the gas mixture during a hydrogenation reaction mixture may vary widely and may lie, for example, in the range 1 to 30 square meters per gram. Surface area for promoted iron catalysts lie between about 3 and 12 square meters per gram although the larger the surface area the larger the rate of reaction. Electron micrographs of titanium-iron alloys show that repeated hydriding and dehydriding, as in the conditioning technique, causes the metal to develop multiple surface cracks, and it is likely that the presence of these microscopic cracks contribute to the active surface area available for catalytic reaction. This continual development of cracks causes the surface area to increase with use and may offset any long-term deactivation resulting from catalytic use.

As mentioned previously, increasing the titanium content of the alloys improves ammonia production. It is known that TiFe is an intermetallic compound which reacts reversibly with hydrogen to form titanium iron hydride, $Ti_1Fe_1H_{1.04}$ and/or $TiFeH_{1.95}$, which is thermally unstable in that it decomposes rapidly at room temperature and atmospheric pressure. It is clear that when the titanium content is increased substantially beyond the 1-to-1 ratio present in TiFe, the hydrided alloy forms the unstable titanium iron hydride as a first component and titanium dihydride as a second component which is more thermally stable in that its decomposition temperature is about 400° C. at atmospheric pressure. It may be that the titanium dihydride in the catalyst plays an important role in increasing the production of ammonia, but the invention is not bound by this or any other theory. With respect to hydrogenation of carbon dioxide and carbon monoxide, it has been found as part of the invention that the $Ti_{1.1}Fe_1$ alloy is more effective than the $Ti_3Fe$ alloy.

The temperatures and pressures of the hydrogenation reactions of the invention may vary widely, although the principal advantage of the invention as it relates to ammonia synthesis is the ability to effect a reasonable rate of reaction at a lower temperature than is currently employed commercially. Hydrogenation of nitrogen, carbon dioxide and carbon monoxide have been carried out in the presence of the titanium-iron alloys at 200° C. to 300° C. and 100 psig. In the ammonia synthesis increased pressure favors the equilibrium yield and therefore one will use whatever maximum pressure is economical or is otherwise desired under the circumstances. It has been found, for example, that at 300° C. ammonia production is increased by a factor of about 20 when the pressure is increased from 100 psi to 500 psi. Higher pressures of 100 to 1000 atmospheres, as used in present commercial production with promoted iron catalysts, may also be employed.

The titanium-iron alloys may be used in granular form as a catalyst bed, or the alloys may be finely divided and supported in or on a catalyst support. Alternatively the finely divided catalyst and the reaction gases may be blown into the reaction vessel together.

The titanium-iron alloys normally contain small amounts of impurities due to the fact that commercially pure titanium is actually about 99.2% pure. Usual impurities include nitrogen, hydrogen, oxygen, iron and carbon if the alloy has been prepared in a carbon crucible.

Most experiments were carried out in a Berty reactor obtained from Autoclave Engineers. A Berty reactor is in effect an exteriorly insulated stainless steel hollow cylinder provided with a top which can be sealed to the cylinder and provided with an electrical resistance heating device. The cylinder is also provided with two interior thermocouples, gas inlet and outlet fittings and a vacuum fitting. The lower end of the cylinder is fitted interiorly with a small fan which is operated by an external electric motor through a magnetic coupling. A perforated stainless steel container holding the alloy was arranged above the fan in such a manner that operation of the fan would draw the gas in the reactor down through the bed of alloy and then pass it upwardly through an annular space between the holder for the container and the wall of the cylinder. The volume of the cylinder, exclusive of fan, container and holder, was 800 ml.

The gas outlet of the reactor described above was fitted with an infra-red analyzer (Beckman 4250) for determining the composition of the gas from the reactor.

EXAMPLE 1

About 95 grams of coarsely crushed $Ti_{1.1}Fe_1$ was placed in the perforated container in the reactor, the heater was turned on and the vacuum pump was started. When the temperature reached about 400° C. the vacuum pump was turned off and the reactor was pressurized with hydrogen to about 65 atmospheres pressure. After 12 hours the vacuum pump was turned on and the reactor was evacuated for several hours. The reactor was again filled with hydrogen to about 65 atmospheres pressure and left for another 12 hours. The hydrogen gas is analyzed by the infra-red analyzer after each treatment. If no impurities show then the catalyst has been activated. Water disappearance from the hydrogen indicates that the catalyst is clean or activated since an oxide film prevents hydrogen penetration of the alloy. If the hydride form is desired it is cooled to reaction temperature and again filled with hydrogen pressure which will saturate the catalyst with hydrogen. This is accompanied by a large pressure drop and a large heat evolution.

The pressure was then reduced and nitrogen was admitted to form a mixture in which the ratio of nitrogen molecules to hydrogen molecules was 1:3 and the pressure was 1200 psi. The temperature was raised to 300° C. and this condition was maintained with the fan operating. After one-half hour the contents of the reactor were analyzed with the infra-red analyzer and was found to contain ammonia. Several runs were made using generally the same procedure. In those runs where maximum ammonia was produced, the ammonia content of the gas after one-half hour was between 3 and 5%. The theoretical equilibrium yield under these conditions is 9%. These yields were obtained under conditions where mass transfer to the catalytic surface was probably controlling and therefore represent minimum values. The surface area as measured by nitrogen adsorption was approximately 1. $m^2/gm$ which is low for ammonia catalysts.

What is claimed is:

1. A method of synthesizing compounds by hydrogenation of benzene which comprises mixing benzene with hydrogen gas and contacting the mixture with a catalyst comprising a solid titanium-iron alloy which is in a form capable of reversible conversion between metallic and hydrided states, at a temperature and pressure at which the catalyst promotes the hydrogenation reaction, and wherein the alloy is selected from the group consisting of binary alloys, ternary alloys and quaternary alloys, where the major components are iron and titanium, and wherein the third component in the ternary alloy and the fourth component in the quaternary alloy are metals or compounds of metals.

* * * * *

UNITED STATES PATENT AND TRADEMARK OFFICE
CERTIFICATE OF CORRECTION

PATENT NO. : 4,560,816

DATED : December 24, 1985

INVENTOR(S) : Milton W. Davis, Jr.

It is certified that error appears in the above-identified patent and that said Letters Patent is hereby corrected as shown below:

First page, 2nd col., first line, "Ozyagcilat" should read --Ozyagcilar"--;

Col. 2, line 21, "on" should read --an--;

Col. 2, line 48, "hydrogenfueled" should read --hydrogen-fueled--; and

Signed and Sealed this

Thirteenth Day of May 1986

[SEAL]

Attest:

DONALD J. QUIGG

Attesting Officer

Commissioner of Patents and Trademarks